(12) United States Patent
Squeri et al.

(10) Patent No.: US 12,369,879 B2
(45) Date of Patent: Jul. 29, 2025

(54) TRANSCUTANEOUS SOUND SENSOR (71) Applicant: W. L. Gore & Associates, Inc., Newark, DE (US)

(72) Inventors: John M. Squeri, Downingtown, PA (US); Christopher J. Vecchio, Philadelphia, PA (US); Minghua Xu, Hockessin, DE (US)

(73) Assignee: W. L. Gore & Associates, Inc., Newark, DE (US)

( * ) Notice: Subject to any disclaimer, the term of this patent is extended or adjusted under 35 U.S.C. 154(b) by 242 days.

(21) Appl. No.: 17/924,029

(22) PCT Filed: May 7, 2021

(86) PCT No.: PCT/US2021/031365
§ 371 (c)(1),
(2) Date: Nov. 8, 2022

(87) PCT Pub. No.: WO2021/226504
PCT Pub. Date: Nov. 11, 2021

(65) Prior Publication Data
US 2023/0218260 A1    Jul. 13, 2023

Related U.S. Application Data

(60) Provisional application No. 63/021,753, filed on May 8, 2020.

(51) Int. Cl.
*A61B 7/02* (2006.01)
*A61B 7/04* (2006.01)

(52) U.S. Cl.
CPC ............... *A61B 7/023* (2013.01); *A61B 7/04* (2013.01)

(58) Field of Classification Search
CPC .................................. A61B 7/023; A61B 7/04
See application file for complete search history.

(56) References Cited

U.S. PATENT DOCUMENTS 5,907,213 A    5/1999  Oshima et al.
8,412,342 B2   4/2013  Zhang et al.
(Continued)

FOREIGN PATENT DOCUMENTS

EP    3848986 A1    7/2021
JP    10-132669 A   5/1998
(Continued)

OTHER PUBLICATIONS

International Preliminary Report on Patentability received for PCT Patent Application No. PCT/US2021/031365, mailed on Nov. 17, 2022, 9 pages.
(Continued)

*Primary Examiner* — Andrew Sniezek (57) ABSTRACT

Embodiments of the present disclosure relate to transcutaneous sound sensors. In at least one embodiment, a transcutaneous sound sensor system comprises a mounting unit and a sound sensor. The mounting unit detachably connects to an electronics unit and mounts to skin on a body. The sound sensor senses sounds originating from inside the body. The sound sensor comprises an in-vivo portion and an ex-vivo portion. The in-vivo portion is configured to be inserted through and placed beneath the skin of the body. In addition, the in-vivo portion has a sound-sensing element configured to produce an electrical signal in response to a mechanical stress or strain on the sound-sensing element. The ex-vivo portion is configured to operably connect to the electronics unit when the electronics unit is connected to the mounting unit.

25 Claims, 3 Drawing Sheets

(56) References Cited

U.S. PATENT DOCUMENTS

| | | |
|---|---|---|
| 2004/0167416 A1 | 8/2004 | Lee |
| 2007/0208390 A1 | 9/2007 | Von Arx et al. |
| 2010/0160756 A1 | 6/2010 | Petisce et al. |
| 2010/0179615 A1* | 7/2010 | Zhang ............... A61N 1/36039 29/25.35 |
| 2010/0217099 A1* | 8/2010 | LeBoeuf ............. A61B 5/6815 600/301 |
| 2016/0095542 A1 | 4/2016 | Simpson et al. |
| 2018/0153476 A1 | 6/2018 | Annoni et al. |
| 2018/0271701 A1* | 9/2018 | Feinsod ............. A61M 5/31511 |
| 2019/0388013 A1 | 12/2019 | Achmann et al. |
| 2021/0351337 A1 | 11/2021 | Ogasahara et al. |

FOREIGN PATENT DOCUMENTS

| | | |
|---|---|---|
| JP | 2003-521972 A | 7/2003 |
| JP | 2012-513821 A | 6/2012 |
| JP | 2018-042797 A | 3/2018 |
| JP | 6501958 B1 | 4/2019 |
| JP | 2020-511240 A | 4/2020 |
| WO | 01/28416 A1 | 4/2001 |
| WO | 2010/075029 A2 | 7/2010 |
| WO | 2018/172349 A1 | 9/2018 |
| WO | 2020/049912 A1 | 3/2020 |

OTHER PUBLICATIONS

International Search Report and Written Opinion received for PCT Patent Application No. PCT/US2021/031365, mailed on Aug. 12, 2021, 13 pages.

Medgadget Editors, "Boston Scientific's Resonate Cardiac Implants with HeartLogic Predict Adverse Events, Now FDA Approved," Medgadget, Sep. 27, 2017, 4 pages.

* cited by examiner

TRANSCUTANEOUS SOUND SENSOR

CROSS-REFERENCE TO RELATED APPLICATION

This application is a national phase application of PCT Application No. PCT/US2021/031365, internationally filed on May 7, 2021, which claims the benefit of Provisional Application No. 63/021,753, filed May 8, 2020, which are incorporated herein by reference in their entireties for all purposes.

FIELD

The present disclosure relates generally to minimally-invasive implantable sensors for medical monitoring. More specifically, the present disclosure relates to the design and use of transcutaneous sound sensors for the monitoring of physiological events in a body. Targets can include sounds from organs such as the heart, lung, and bowel.

BACKGROUND

Traditionally, auscultation involves the use of a stethoscope on bare skin to listen to the internal sounds of a body, such as heart and breath sounds, as well as bowel sounds. These sounds may provide valuable information on the status of the respective circulatory, respiratory, or gastrointestinal (GI) systems.

SUMMARY

The present disclosure relates to a transcutaneous sound sensor system. Exemplary embodiments include but are not limited to the following examples.

In an Example 1, a transcutaneous sound sensor system comprises: a mounting unit configured to detachably connect to an electronics unit and the mounting unit configured to mount on a skin of a body; and a sound sensor configured to sense sounds originated from inside the body, the sound sensor comprising an in-vivo portion and an ex-vivo portion, the in-vivo portion configured to be inserted through and placed beneath the skin of the body, wherein the in-vivo portion has a sound-sensing element configured to produce an electrical signal in response to a mechanical stress or strain on the sound-sensing element, wherein the ex-vivo portion is configured to operably connect to the electronics unit when the electronics unit is connected to the mounting unit.

In an Example 2, the transcutaneous sound sensor system of Example 1, further comprising a device configured to receive and process sound measurements from the electronics unit through a wired or non-wired communication link between the device and the electronics unit.

In an Example 3, the transcutaneous sound sensor system of any one of Examples 1-2, wherein the mounting unit further comprises electrocardiograph (ECG) electrodes configured to measure one or more ECG signals of the body.

In an Example 4, the transcutaneous sound sensor system of any one of Examples 1-3, wherein at least a portion of an outer surface of the in-vivo portion comprises a hydrophilic coating.

In an Example 5, the transcutaneous sound sensor system of any one of Examples 1-4, wherein the sound sensor has a coaxial structure comprising multiple layers.

In an Example 6, the transcutaneous sound sensor system of Example 5, wherein an innermost layer of the sensor is a core conductor.

In an Example 7, the transcutaneous sound sensor system of Example 6, wherein a second layer of the coaxial structure arranged around the innermost layer is a polarized piezo-polymer layer.

In an Example 8, the transcutaneous sound sensor system of Example 6, where a second layer of the coaxial structure arranged around the innermost layer is a piezo-ceramic layer.

In an Example 9, the transcutaneous sound sensor system of any one of Examples 7-8, wherein the second layer is a spiral layer wrapped around the innermost layer.

In an Example 10, the transcutaneous sound sensor system of any one of Examples 7-8, wherein the second layer is a continuous, solid layer arranged around the innermost layer.

In an Example 11, the transcutaneous sound sensor system of any one of Examples 7-10, wherein a third layer arranged around the second layer is a conductor.

In an Example 12, the transcutaneous sound sensor system of Example 11, wherein the third layer is a spiral layer wrapped around the second layer.

In an Example 13, the transcutaneous sound sensor system of any one of Examples 11-12, wherein a fourth layer arranged around the third layer is a protective layer.

In an Example 14, the transcutaneous sound sensor system of any one of Examples 1-13, further comprising the electronics unit.

In an Example 15, a transcutaneous sound sensor comprises: a sound-sensing element configured to be implanted under skin of a subject and configured produce an electrical signal in response to a mechanical stress or strain on the sound-sensing element; a proximal end configured to be releasably and communicatively coupled to an electronics unit; and a protective layer arranged around the sound-sensing element.

In an Example 16, the transcutaneous sound sensor of Example 15, wherein the sound-sensing element surrounds a core conductor.

In an Example 17, the transcutaneous sound sensor of Example 16, wherein the sound-sensing element is spirally wrapped around the core conductor.

In an Example 18, the transcutaneous sound sensor of any one of Examples 15-17, wherein a conductor layer is arranged around the sound-sensing element.

In an Example 19, the transcutaneous sound sensor of Example 18, wherein conductor layer is spirally wrapped around the sound-sensing element.

In an Example 20, the transcutaneous sound sensor of any one of Examples 18-19, wherein the protective layer surrounds the conductor layer.

In an Example 21, the transcutaneous sound sensor of any one of Examples 15-20, wherein at least a portion of an outer surface of the transcutaneous sound sensor comprises a hydrophilic coating.

In an Example 22, the transcutaneous sound sensor of any one of Examples 15-21, wherein the sound-sensing element is formed from a polarized polyvinylidene fluoride (PVDF) film, a PVDF copolymer (e.g., PVDF-TrFE) film, or a piezoceramic material.

In an Example 23, the transcutaneous sound sensor of any one of Examples 15-22, wherein the protective layer is formed from a biocompatible insulation material.

In an Example 24, the transcutaneous sound sensor of Example 23, wherein the biocompatible insulation material is at least one of: a parylene, a silicon rubber, or ePTFE.

In an Example 25, a method of treatment using a transcutaneous sound sensor system, the method comprising: coupling an electronics unit to a sound sensor, the sound sensor configured to sense sounds originating from inside a subject, the sounds sensor comprising an in-vivo portion arranged beneath a skin surface of the subject and an ex-vivo portion arranged exterior to the skin surface; receiving signals from the electronics unit corresponding to sound measurements sensed by the sound sensor; and processing the received signals to determine characteristics of the sound measurements.

In an Example 26, the method of Example 25, further comprising implanting the in-vivo portion beneath the skin surface and the ex-vivo portion exterior to the skin surface.

In an Example 27, the method of Example 25, further comprising correlating the characteristics of the sound measurements to specific parts of the subject.

The foregoing Examples are just that and should not be read to limit or otherwise narrow the scope of any of the inventive concepts otherwise provided by the instant disclosure. While multiple examples are disclosed, still other embodiments will become apparent to those skilled in the art from the following detailed description, which shows and describes illustrative examples. Accordingly, the drawings and detailed description are to be regarded as illustrative in nature rather than restrictive in nature.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

FIG. 4 is block diagram of an electronics unit depicted in FIG. 2 and the additional device depicted in FIG. 1, in accordance with embodiments of the subject matter disclosed herein As the terms are used herein with respect to ranges of measurements "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like.

This disclosure is not meant to be read in a restrictive manner. For example, the terminology used in the application should be read broadly in the context of the meaning those in the field would attribute such terminology.

With respect terminology of inexactitude, the terms "about" and "approximately" may be used, interchangeably, to refer to a measurement that includes the stated measurement and that also includes any measurements that are reasonably close to the stated measurement. Measurements that are reasonably close to the stated measurement deviate from the stated measurement by a reasonably small amount as understood and readily ascertained by individuals having ordinary skill in the relevant arts. Such deviations may be attributable to measurement error or minor adjustments made to optimize performance, for example. In the event it is determined that individuals having ordinary skill in the relevant arts would not readily ascertain values for such reasonably small differences, the terms "about" and "approximately" can be understood to mean plus or minus 10% of the stated value.

DETAILED DESCRIPTION

Persons skilled in the art will readily appreciate that various aspects of the present disclosure can be realized by any number of methods and apparatus configured to perform the intended functions. It should also be noted that the accompanying drawing figures referred to herein are not necessarily drawn to scale but may be exaggerated to illustrate various aspects of the present disclosure, and in that regard, the drawing figures should not be construed as limiting.

As stated above, conventional auscultation uses a stethoscope on bare skin to listen to internal sounds of a subject. Auscultation, however, has drawbacks. For example, auscultation is a skill that often requires substantial clinical experience, a fine stethoscope and good listening skills. This is because the sound volume produced by a traditional acoustic stethoscope is typically low. Ambient noise, individual hearing limitations and variations of auscultation points can all influence the sounds one can hear.

Various electronic stethoscopes have been developed to improve on conventional stethoscopes. For example, electronic stethoscopes may electrically amplify faint sounds from the body, improve sound pickup via advanced transducer designs, and apply computer-aided processing techniques such as noise cancellation and digital analysis. However, external listening to internal sounds of a subject using these electronic stethoscopes may still present problems.

For example, sounds can be transmitted easily and efficiently inside the body because of the abundance of liquid in the body. However, sound waves may be reflected, attenuated and/or distorted by the skin before the sound ways reach the stethoscope transducer surface. The poor sound transmission at the boundary of the skin between the organ producing the sound and the stethoscope transducer surface may result in a failure to capture desired information. Moreover, externally positioned sound transducers may sense undesired ambient noise. Further, the variation of points on the body's surface at which auscultation is performed can influence the sounds that the sensors can hear, which may add uncertainty to the comparison of sound patterns collected over extended periods of time.

To reduce or avoid the problems associated with conventional auscultation, the embodiments disclosed herein describe a transcutaneous sound sensor.

Figure 1:
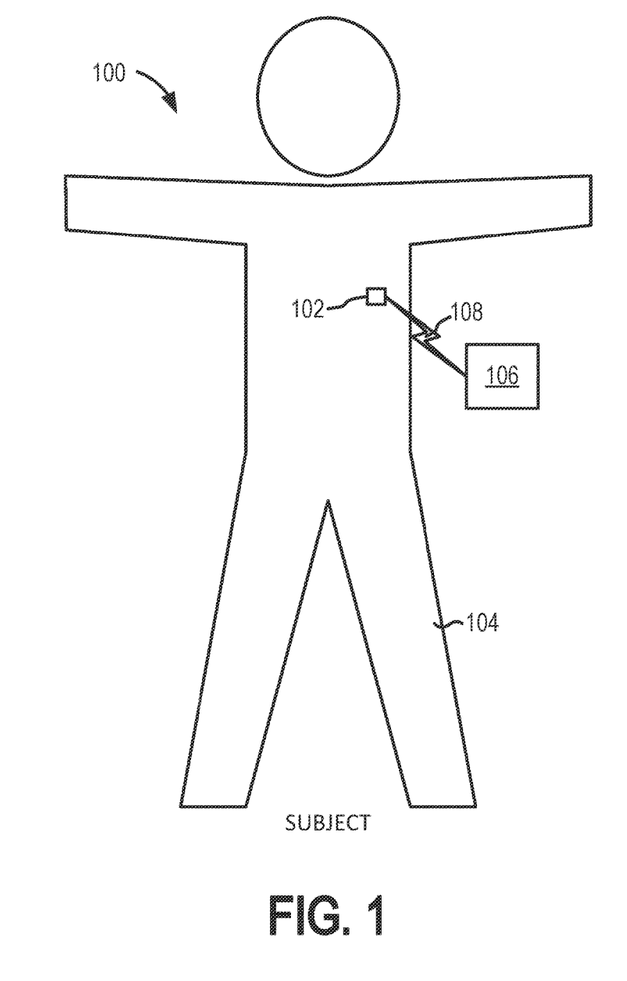
FIG. 1 is a schematic illustration of a system including a transcutaneous sound sensor, in accordance with embodiments of the disclosure.

FIG. 1 is a schematic illustration of a system 100 including a transcutaneous sound sensor 102. As shown in FIG. 1, the transcutaneous sound sensor 102 is configured to be arranged on the body of a subject 104. The transcutaneous sound sensor 102 can be arranged on different areas of the subject 104 based on the different sounds to be sensed by the transcutaneous sound sensor 102. For example, the transcutaneous sound sensor 102 may be arranged on the left portion of the chest of the subject 104 in the event heart sounds are to be sensed by the transcutaneous sound sensor 102. As another example, the transcutaneous sound sensor 102 may be placed on the chest (e.g., the right portion of the chest of the subject 104) in the event respiratory sounds are to be sensed by the transcutaneous sound sensor 102. As even another example, the transcutaneous sound sensor 102 may be placed on the abdomen of the subject 104 in the event digestive sounds are to be sensed by the transcutaneous sound sensor 102. In at least some embodiments, multiple transcutaneous sound sensors 102 may be arranged on a subject to sense different types of sounds produced by the subject 104. In embodiments, the subject 104 may be a human, a dog, a pig, and/or any other animal producing sounds that can be sensed. For example, the subject 104 may be a human patient.

The transcutaneous sound sensor 102 is configured to sense sounds produced by the subject 104. For example, the transcutaneous sound sensor 102 may sense heart sounds and/or other sounds associated with the subject's 104 circulatory system, respiratory sounds associated with the subject's 104 respiration system, digestive sounds associated with the subject's 104 digestive system, and/or the like. In at least some embodiments, the transcutaneous sound sensor 102 may also include electrodes configured to sense electrocardiogram signals. Once the sounds and/or ECG signals are sensed by the transcutaneous sound sensor 102, the transcutaneous sound sensor 102 may store and/or process the sounds and/or ECG signals to determine characteristics of the sensed sounds and/or ECG signals.

In embodiments, the transcutaneous sound sensor 102 is configured to be communicatively coupled to another device (AD) 106 via a communication link 108. The AD 106 may be configured to receive, store, and/or process signals (e.g., sounds and/or ECG signals) sensed by the transcutaneous sound sensor 102. In at least some embodiments, the AD 106 may also perform a power management function for the transcutaneous sound sensor 102. For example, the AD 106 may wake the transcutaneous sound sensor 102, sleep the transcutaneous sound sensor 102, and/or direct the transcutaneous sound sensor 102 to sense, store, process, and/or transmit signals corresponding to sounds produced by the subject 104. Embodiments of the AD 106 may be any type of device having computing capabilities such as, for example, a smartphone, a tablet, a notebook, or other portable or non-portable computing device.

The communication link 108 may be, or include, a wired link (e.g., a link accomplished via a physical connection) or a non-wired link such as, for example, a short-range radio link, such as Bluetooth, IEEE 802.11, near-field communication (NFC), WiFi, a proprietary wireless protocol, and/or the like. The term "communication link" may refer to an ability to communicate some type of information in at least one direction between at least two devices and should not be understood to be limited to a direct, persistent, or otherwise limited communication channel. That is, according to embodiments, the communication link 108 may be a persistent communication link, an intermittent communication link, an ad-hoc communication link, and/or the like. The communication link 108 may refer to direct communications between the transcutaneous sound sensor 102 and the AD 106, and/or indirect communications that travel between the transcutaneous sound sensor 102 and the AD 106 via at least one other device (e.g., a repeater, router, hub, and/or the like). The communication link 108 may facilitate uni-directional and/or bi-directional communication between the transcutaneous sound sensor 102 and the AD 106. Data and/or control signals may be transmitted between the transcutaneous sound sensor 102 and the AD 106 to coordinate the functions of the transcutaneous sound sensor 102 and/or the AD 106. In embodiments, subject data may be downloaded from one or more of the transcutaneous sound sensor 102 and the AD 106 periodically or on command. The clinician and/or the subject 104 may communicate with the transcutaneous sound sensor 102 and/or the AD 106, for example, to initiate, terminate and/or modify sensing, storing, processing and/or transmitting signals.

The illustrative system 100 shown in FIG. 1 is not intended to suggest any limitation as to the scope of use or functionality of embodiments of the present disclosure. The illustrative system 100 should not be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are within the ambit of the subject matter disclosed herein.

Figure 2:
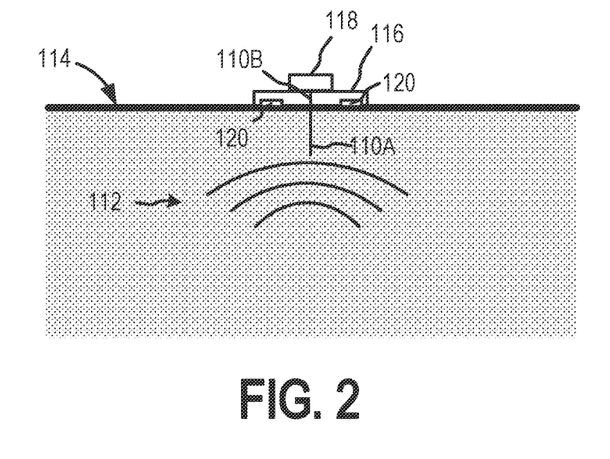
FIG. 2 is a schematic illustration of the transcutaneous sound sensor, in accordance with at least one embodiment of the present disclosure.

FIG. 2 is a schematic illustration of the transcutaneous sound sensor 102. In at least some embodiments, the transcutaneous sound sensor 102 includes a sound sensor 110 comprising an in-vivo portion 110A communicatively coupled to an ex-vivo portion 110B. As such, any signals sensed by the in-vivo portion 110A can be transmitted to the ex-vivo portion 110B As illustrated, the in-vivo portion 110A is configured to be arranged beneath the surface 114 of the skin of the subject 104 and is configured to sense sounds 112 produced by the subject 104. To arrange the in-vivo portion 110A beneath the surface 114, the in-vivo portion 110A may be a sensor wire where a tip of the sensor wire is inserted into the subject 104. In embodiments, the sensor wire may be inserted into the subject 104 with the aid of an insertion device (e.g., a needle), which is removed after the sensor wire is inserted into the subject 104. Once arranged beneath the surface 114, the in-vivo portion 110A will have minimal movement. As such, the transcutaneous sound sensor 102 reduces a drawback of auscultation, namely, the variation in points on the surface 114 at which a medical professional may listen for a specific sound. As such, the in-vivo portion 110A is more likely to be able to sense changes in waveforms in sounds 112. Furthermore, sounds 112 can be sensed and recorded on a continuous basis instead of only periodically as is the case with auscultation. Continuous monitoring may be especially beneficial when recording sounds associated with chronic diseases.

The sounds 112 sensed by the in-vivo portion 110A include but are not limited to: heart sounds and/or other sounds associated with the subject's 104 circulatory system, respiratory sounds associated with the subject's 104 respiration system, digestive sounds associated with the subject's 104 digestive system, and/or the like. Because the in-vivo portion 110A is arranged beneath the surface 114 of the skin, the surface 114 does not interfere (e.g., reflect, attenuate, and/or distort) with sounds 112 produced by the subject 104. Conversely, sounds sensed by sensors, such as stethoscopes, may reflected, attenuated and/or distorted due to the surface 114. Furthermore, the in-vivo portion 110A is less likely to sense ambient noise than if the in-vivo portion 110A were located on the surface 114. Additional exemplary characteristics of the in-vivo portion 110A are described in more detail below in relation to FIGS. 3A-3B.

The ex-vivo portion 110B is not arranged beneath the surface 114 of the subject's 104 skin and is detachably coupled to a mounting unit 116 and/or an electronics unit 118. Because the ex-vivo portion 110B is coupled to an electronics unit 118 arranged external the surface 114, the transcutaneous sound sensor 102 does not have some of the drawbacks of a device located completely in-vivo, such as limited access, power, storage, processing, and transmission capabilities. Instead, the processor, memory, communication components, etc. included in the electronics unit 118 are more easily accessible than if the transcutaneous sound sensor 102 were located completely in-vivo. Furthermore, by only having a portion of the transcutaneous sound sensor 102 arranged beneath the surface 114 (i.e., the in-vivo portion 110A), the transcutaneous sound sensor 102 will elicit less of a foreign body response than if the entirety of the transcutaneous sound sensor 102 were located beneath the surface 114.

The mounting unit 116 may be arranged on the surface 114 in a manner that allows movement of the surface 114 underneath the mounting unit 116. In some embodiments, the mounting unit 116 may be formed of a material and arranged on the surface 114 so the mounting unit 116 moves with flexion of the surface 114. For example, the mounting unit 116 may be made of a flexible material and can be adhered to the surface 114 and/or sutured to the surface 114. Exemplary adhesives include but are not limited to silicon-based adhesives and/or acrylic-based adhesives. In other embodiments the mounting unit 116 may be formed from a material and arranged on the surface 114 so the mounting unit 116 allows bending and flexing movements of the surface 114 but does not change its location on the surface with flexion of the surface 114.

In at least some embodiments, the electronics unit 118 is detachably coupled via a wired or a non-wired connection to the ex-vivo portion 110B of the sound sensor 110. Via the coupling between the electronics unit 118 and the ex-vivo portion 110B, the electronics unit 118 is configured to receive signals corresponding to sounds sensed by the in-vivo portion 110A. Additionally, the electronics unit 118 may be communicatively coupled to the AD 106. As such, the electronics unit 118 may store, process, and/or transmit the signals to AD 106 after receiving signals sensed by the in-vivo portion 110A. In at least some embodiments, the AD 106 may direct the electronics unit 118 to sense, store, process, and/or transmit signals corresponding to sounds produced by the subject 104. Exemplary components of the electronics unit 118 are described in more detail below in relation to FIG. 4.

In at least some embodiments, the mounting unit 116 may be detachably coupled via a wire or a non-wired connection to the ex-vivo portion 110B and the electronics unit 118 may be detachably coupled to the mounting unit 116. As such, the electronics unit 118 may receive signals from the ex-vivo portion 110B via the mounting unit 116. In embodiments, the electronics unit 118 may be releasably coupled to the mounting unit 116 via a snap, connector, and/or other type of fastener.

Additionally, or alternatively, the mounting unit 116 may include one or more electrodes 120 configured to sense one or more electrocardiograph ECG signals of the subject 104. The electronics unit 118 may detachably connect to the electrodes 120 directly or via the mounting unit 116. Accordingly, the electronics unit 118 may receive the signals sensed by the electrodes 120 and store, process, and/or transmit the signals to AD 106. In at least some embodiments, the electronics unit 118 may align the ECG signals with heart sounds sensed by the in-vivo portion 110A. The sensed ECG signals aligned with the heart sounds may be used to identify and analyze certain physiological characteristics of the subject 104.

Figure 3A:
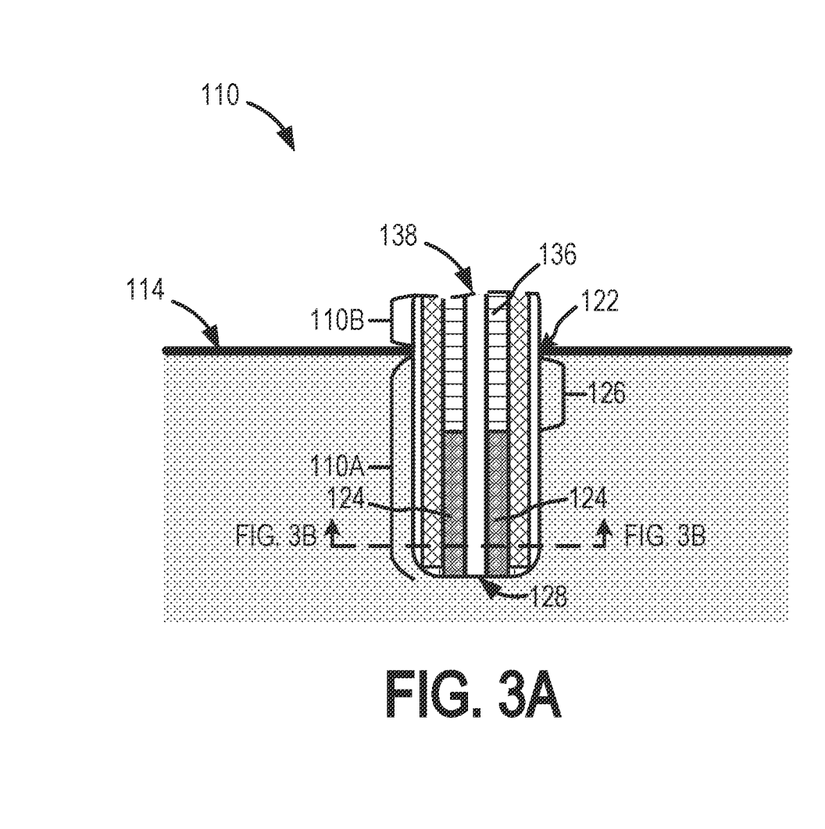
FIG. 3A is a side sectional view of a portion of the sound sensor depicted in FIG. 2, in accordance with at least one embodiment of the present disclosure.
Figure 3B:
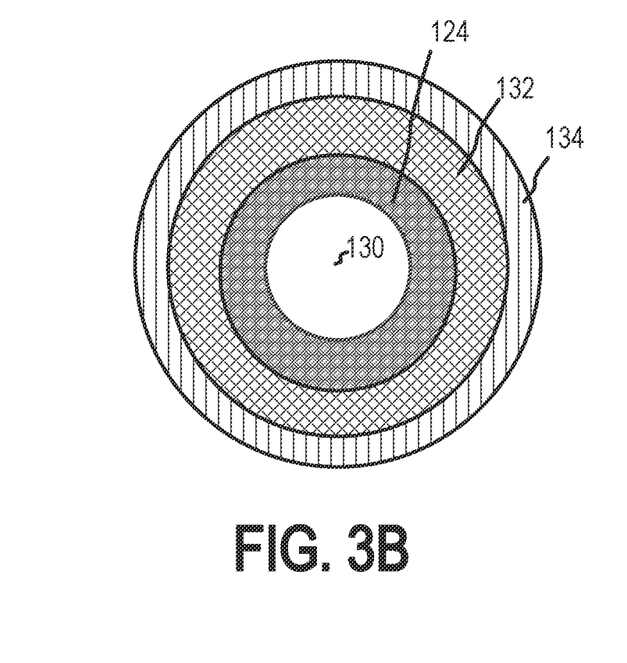
FIG. 3B is an end on sectional view of the sound sensor depicted in FIG. 2, in accordance with at least one embodiment of the present disclosure.

FIG. 3A depicts a side sectional view of a portion of the sound sensor 110 and FIG. 3B depicts an end on sectional view of the sound sensor 110. As illustrated, the sound sensor 110 includes an in-vivo portion 110A arranged beneath the surface 114 and an ex-vivo portion 110B connected to the in-vivo portion 110A and arranged exterior the surface 114. As stated above, the ex-vivo portion 110B may be detachably coupled to the electronics unit 118 (of FIG. 2). As such, the electronics unit 118 is configured to receive sensed sounds from the in-vivo portion 110A via the ex-vivo portion 110B.

The in-vivo portion 110A is inserted through the surface 114 at a site 122. As stated above, the in-vivo portion 110A may be inserted through the surface 114 using an insertion device, such as a needle. The in-vivo portion 110A inserted beneath the surface 114 includes a sound-sensing element 124. The sound-sensing element 124 is configured to sense sounds produced by a subject 104 (shown in FIG. 2). For example, the sound-sensing element 124 may include a diaphragm that distorts as the acoustical energy of a sound wave produced by the subject 104 passes through the diaphragm and mechanically stresses or strains the diaphragm. Sounds produced by various parts of the subject 104 may have different characteristics, such as different durations, frequencies, amplitudes, and/or quality, and, therefore, produce different mechanical stresses or strains on the diaphragm, each of which may be correlated to specific parts of the subject 104. The sound-sensing element 124 can also include a transducer that produces varying electrical signals in response to the different distortions of the diaphragm as a result of the different mechanical stresses or strains. As such, when a sound wave (e.g., a sound 112) contacts the sound-sensing element 124, the sound-sensing element 124 experiences a stress or a strain and in response produces an electrical signal, which can be correlated to a part of the subject 104 and transmitted by the sound sensor 110 to the electronics unit 118. In at least some embodiments, the sound-sensing element 124 is a piezo-polymer layer, which is formed from a material such as, for example, a polyvinylidene fluoride (PVDF) film or a PVDF copolymer (e.g., PVDF-TrFE) film, which exhibits the piezoelectric effect when polarized.

The remainder 126 of the in-vivo portion 110A separates the sound-sensing element 124 from the surface 114 to reduce the likelihood of ambient and/or reflective sounds interfere with sensing sounds by the sound-sensing element 124. In at least some embodiments, a hydrophilic coating may be disposed on the tip 128 of the in-vivo portion 110A to improve the sensing capabilities of the sound-sensing element 124.

As illustrated in FIGS. 3A-3B, the sound sensor 110 may have a coaxial structure. For example, the sound senor 110 may include a core 130 surrounded by a plurality of layers (e.g., the sound-sensing element 124, a conductive layer 132, and/or a protective layer 134).

In at least some embodiments, the core 130 can be an elongate conductor that is a tube, a solid wire, or a stranded wire for flexibility. For example, the core 130 may be comprised of: platinum, titanium, MP35N alloy, and/or any other type of conductive material.

Surrounding the tip portion of the core 130 can be the sound-sensing element 124. In the illustrated embodiment, the sound-sensing element 124 can be formed around the core 130 by circumferential disposition. In alternative embodiments, the sound-sensing element 124 can be spirally wrapped around the core 130 using single or multiple layers of piezo-polymer tape.

An electrical insulation layer 136 may abut an end of the sound-sensing element 124 and/or separate the core 130 from a conductive layer 132. Similar to the sound-sensing element 124, the electrical insulation layer 136 may formed around the core 130 by circumferential disposition or can be spirally wrapped around the core 130 using single or multiple layers of insulation tapes. In some embodiments, the electrical insulation layer 136 is formed from electrical insulation materials such as an ePTFE film. In an alternative embodiment, the electrical insulation layer 136 is merely an extension of the sound-sensing element 124 and can be formed from a piezo-polymer material without being polarized.

Surrounding the sound-sensing element 124 and the electrical insulation layer 136 is another conductive layer 132. In some embodiments, the conductive layer 132 is a thin metallic layer, which may be a thin film layer formed form any suitable biocompatible conductive material such as, for example, titanium, platinum, gold, and/or the like. In some embodiments, the conductive layer 132 can be formed by circumferential disposition of conductive material on the external surfaces of the sound-sensing element 124 and the electrical insulation layer 136. In alternative embodiments, the conductive layer 132 can be composed of braided strands of metal, a non-braided spiral winding of metal tape, or a layer of conducting polymer. In some embodiments, the proximal ends 138 of the core 130 and the conductive layer 132 are not covered by insulation material and serve electrodes to connect the sound sensor 110 to the electronics unit 118.

In at least some embodiments, a protective layer 134 may surround the conductive layer 132. In some embodiments, the protective layer 134 may be formed from any suitable biocompatible insulation material such as parylene, silicon rubber, or ePTFE. Additionally, or alternatively, the protective layer 134 may comprise a hydrophilic coating, which improves sound transmission to the sound-sensing element 124.

Figure 4:
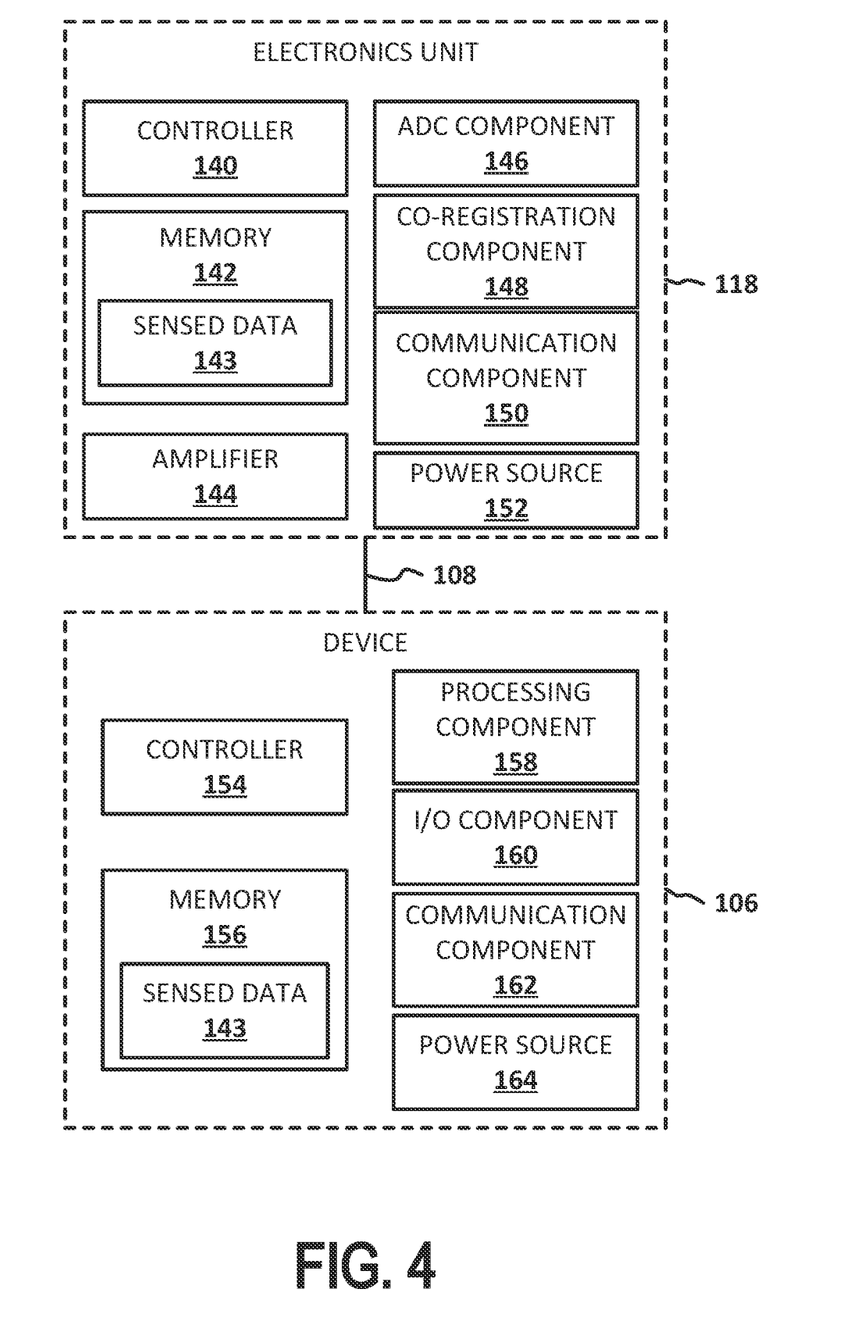

FIG. 4 is block diagram of an electronics unit 118 of the transcutaneous sound sensor depicted in FIG. 2 and the additional device (AD) 106 depicted in FIG. 1. As stated above, the electronics unit 118 may be releasably and/or communicatively connected to the mounting unit and/or may be releasably and/or communicatively coupled to the sound sensor 110 and/or the electrodes 120.

In at least some embodiments, the electronics unit 118 includes a controller 140, a memory 142 including sensed data 143, an amplifier 144, an analog-to-digital component (ADC) 146, a co-registration component 148, a communication component 150, and/or a power source 152.

The controller 140 may include, for example, a processing unit, a pulse generator, and/or the like. The controller 140 may be any arrangement of electronic circuits, electronic components, processors, program components and/or the like configured to store and/or execute programming instructions, to direct the operation of the other functional components of the electronics unit 118. For example, the controller 140 may instruct the sound sensor 110 (of FIGS. 2-3B) to sense one or more sounds of a subject (e.g., the subject 104), to instruct the amplifier 144 to amplify any sound signals sensed by the sound sensor 110, to instruct the ADC 146 to convert any sounds signals sensed by the sound sensor 110 from analog signals to digital signals, to store any sensed data 143, to instruct the communication component 150 to transmit any data corresponding to sounds sensed by the sound sensor 110 and/or the like, and may be implemented, for example, in the form of any combination of hardware, software, and/or firmware.

In embodiments, the controller 140 may be, include, or be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more central processing units (CPUs), software, hardware, firmware, or any combination of these and/or other components. According to embodiments, the controller 140 may include a processing unit configured to communicate with memory to execute computer-executable instructions stored in the memory. Although the controller 140 is referred to herein in the singular, the controller 140 may be implemented in multiple instances, distributed across multiple computing devices, instantiated within multiple virtual machines, and/or the like.

The controller 140 may also be configured to store information (e.g., sensed data 143) in the memory 142 and/or access information (e.g., sensed data 143) from the memory 142. The controller 140 may execute instructions and perform desired tasks as specified by computer-executable instructions stored in the memory 142.

In embodiments, the memory 142 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory stores computer-executable instructions for causing the processor to implement aspects of embodiments of system components discussed herein and/or to perform aspects of embodiments of methods and procedures discussed herein.

The computer-executable instructions may include, for example, computer code, digital signal processing, machine-useable instructions, and the like such as, for example, program components capable of being executed by one or more processors associated with the computing device. Program components may be programmed using any number of different programming environments, including various languages, development kits, frameworks, and/or the like. Some or all of the functionality contemplated herein may also, or alternatively, be implemented in hardware and/or firmware.

As stated above, the amplifier 144 may amplify any sounds sensed by the sound sensor 110 and the ADC 146 may convert any sounds sensed by the sound sensor 110 from analog signals to digital signals. Additionally, or alternatively, the amplifier 144 may amplify any ECG signals sensed by the electrodes 120 and the ADC 146 may convert any ECG signals sensed by the electrodes 120 from analog signals to digital signals. And, the memory 142 may store any such sensed data 143.

In at least some embodiments, the co-registration component 148 may align sensed sounds with sensed ECG signals. For example, the signals may by synchronously sampled and a time shift may be applied as a correction to one or both signals. The time shift adjusts for delays in propagation time to the sensor due to the finite speed of sound. After the signals are aligned, the aligned signals may be stored as sensed data 143.

The communication component 150 may be configured to communicate (i.e., send and/or receive signals) with the AD 106 and/or any other device. For example, the sensed data 143 may be transmitted to the AD 106 for processing and/or storage. In embodiments, the communication component 150 may include, for example, circuits, program components, antennas, and one or more transmitters and/or receivers for communicating wirelessly with one or more other devices such as, for example, the AD 106. According to various embodiments, the communication component 150 may include one or more transmitters, receivers, transceivers, transducers, and/or the like, and may be configured to facilitate any number of different types of wireless communication such as, for example, radio-frequency (RF) communication, microwave communication, infrared or visual spectrum communication, acoustic communication, inductive communication, conductive communication, and/or the like. The communication component 150 may include any combination of hardware, software, and/or firmware configured to facilitate establishing, maintaining, and using any number of communication links.

The power source 152 provides electrical power to the other operative components (e.g., the controller 140, the memory 142, the amplifier 144, the ADC 146, the co-registration component 148, and the communication component 150), and may be any type of power source suitable for providing the desired performance and/or longevity requirements of the electronics unit 118. In various embodiments, the power source 152 may include one or more batteries, which may be rechargeable (e.g., using an external energy source). The power source 152 may include one or more capacitors, energy conversion mechanisms, and/or the like. Additionally, or alternatively, the power source 152 may harvest energy from a subject (e.g., the subject 104) (e.g. motion, heat, biochemical) and/or from the environment (e.g. electromagnetic).

As shown in FIG. 2, the AD 106 is communicatively coupled to the electronics unit via the communication link 108 and includes a controller 154, a memory 156 including sensed data 143, a processing component 158, an I/O component 160, a communication component 162, and a power source 164. Similar to the controller 140, the controller 154 may include, for example, a processing unit, a pulse generator, and/or the like. The controller 154 may be any arrangement of electronic circuits, electronic components, processors, program components and/or the like configured to store and/or execute programming instructions, to direct the operation of the other functional components of the AD 106, to store data received by the AD 106 from the electronics unit 118, and the like, and may be implemented, for example, in the form of any combination of hardware, software, and/or firmware.

In embodiments, the controller 154 may be, include, or be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more central processing units (CPUs), software, hardware, firmware, or any combination of these and/or other components. According to embodiments, the controller 154 may include a processing unit configured to communicate with memory 156 to execute computer-executable instructions stored in the memory. Although the controller 154 is referred to herein in the singular, the controller 154 may be implemented in multiple instances, distributed across multiple computing devices, instantiated within multiple virtual machines, and/or the like.

The controller 154 may also be configured to store information (e.g., sensed data 143) in the memory 156 and/or access information (e.g., sensed data 143) from the memory 156. The controller 154 may execute instructions and perform desired tasks as specified by computer-executable instructions stored in the memory 156. In embodiments, for example, the controller 154 may be configured to instantiate, by executing instructions stored in the memory 156.

In embodiments, the memory 156 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory stores computer-executable instructions for causing the processor to implement aspects of embodiments of system components discussed herein and/or to perform aspects of embodiments of methods and procedures discussed herein.

The computer-executable instructions may include, for example, computer code, machine-useable instructions, and the like such as, for example, program components capable of being executed by one or more processors associated with the computing device. Program components may be programmed using any number of different programming environments, including various languages, development kits, frameworks, and/or the like. Some or all of the functionality contemplated herein may also, or alternatively, be implemented in hardware and/or firmware.

The processing component 158 may be configured to process the sensed data 143 received from the electronics unit 118 and cause the I/O component 160 to present a representation of the sensed data 143. According to embodiments, the processing component 158 may be configured to interpret, analyze, and/or otherwise process the sensed data 143 prior to presenting representations thereof. In embodiments, the processing component 158 may provide, via a graphical user interface (GUI), interactive representations of the sensed data 143. Representations of the sensed data 143 may include, for example, parameter values, indications of diagnoses, graphs, charts, anatomical maps, images (e.g., ECG images), and/or the like. According to embodiments, the processing component 158 may also be configured to receive, via a GUI, inputs from a user that indicate parameter settings for a particular sensing task. That is, for example, the GUI may facilitate user control of any number of aspects of operation of the AD 106.

The I/O component 160 in conjunction with the processing component 158 may include and/or be coupled to a user interface configured to present information to a user or receive indication from a user. For example, the I/O component 160 may include and/or be coupled to a display device, a speaker, a printing device, and/or the like, and/or an input component such as, for example, a microphone, a joystick, a satellite dish, a scanner, a printer, a wireless device, a keyboard, a pen, a voice input device, a touch input device, a touch-screen device, an interactive display device, a mouse, and/or the like. As stated above, the I/O component 160 may be used to present and/or provide an indication of any of the sensed data 143. According to embodiments, for example, the I/O component 160 may include one or more visual indicators (e.g., single-color LED lights, multi-color LED lights, a flexible digital display device, and/or the like) configured to provide information to a user (e.g., by illuminating, flashing, displaying data, etc.).

The communication component 162 may be configured to communicate (i.e., send and/or receive signals) with the electronics unit 118 and/or any other device. For example, the communication component 162 may be configured to receive the sensed data 143 from the electronics unit 118. Additionally, or alternatively, the communication component 162 may be configured to send commands to the electronics unit 118 and/or send the sensed data 143 to another device (not shown) for processing and/or storage.

According to various embodiments, the communication component 162 may include one or more transmitters, receivers, transceivers, transducers, and/or the like, and may be configured to facilitate any number of different types of wireless communication such as, for example, radio-frequency (RF) communication, microwave communication, infrared or visual spectrum communication, acoustic communication, inductive communication, conductive communication, and/or the like. The communication component 162 may include any combination of hardware, software, and/or firmware configured to facilitate establishing, maintaining, and using any number of communication links.

The power source 164 provides electrical power to the other operative components (e.g., the controller 154, the memory 156, the processing component 158, the I/O component 160, and the communication component 162), and may be any type of power source suitable for providing the desired performance and/or longevity requirements of the AD 106. In various embodiments, the power source 164 may include one or more batteries, which may be rechargeable (e.g., using an external energy source). The power source 164 may include one or more capacitors, energy conversion mechanisms, and/or the like. In embodiments, the power source 164 may transfer power to the power source 152 using a wireless or non-wireless connection (e.g., via conduction, induction, radio-frequency, etc.). Because the electronics unit 118 may be a small device, the power source 152 may not be capable of storing a lot of power and, therefore, the longevity of the electronics unit 118 may be increased via power transfer from the AD 106 to the electronics unit 118.

The diagram shown in FIG. 4 is not intended to suggest any limitation as to the scope of use or functionality of embodiments of the present disclosure. The diagram also should not be interpreted as having any dependency or requirement related to any single component or combination of components illustrated therein. Additionally, various components depicted in FIG. 4 may be, in embodiments, integrated with various ones of the other components depicted therein (and/or components not illustrated), all of which are within the ambit of the present disclosure.

The embodiments disclosed herein have been described above both generically and with regard to specific embodiments. It will be apparent to those skilled in the art that various modifications and variations can be made in the embodiments without departing from the scope of the disclosure. Thus, it is intended that the embodiments cover the modifications and variations of this disclosure provided they come within the scope of the appended claims and their equivalents

What is claimed is:

1. A transcutaneous sound sensor system comprising:
a mounting unit detachably connectable to an electronics unit and mountable on a skin of a body; and
a sound sensor configured to sense sounds originated from inside the body, the sound sensor comprising an in-vivo portion and an ex-vivo portion, the in-vivo portion being insertable through and placed beneath the skin of the body, wherein the in-vivo portion has a sound-sensing element that produces an electrical signal in response to a mechanical stress or strain on the sound-sensing element, wherein the ex-vivo portion is arrangeable exterior to the skin and is operably connected to the electronics unit when the electronics unit is connected to the mounting unit,
wherein the sound sensor has a coaxial structure comprising multiple layers, an innermost layer of the sound sensor is a core conductor, a second layer of the coaxial structure arranged around the innermost layer at the in-vivo portion of the sound sensor includes a polarized piezo-polymer layer, and the second layer of the coaxial structure arranged around the innermost layer at the ex-vivo portion of the sound sensor includes an electrically insulating material.

2. The transcutaneous sound sensor system of claim 1, further comprising a device configured to receive and process sound measurements from the electronics unit through a wired or non-wired communication link between the device and the electronics unit.

3. The transcutaneous sound sensor system of claim 1, wherein the mounting unit further comprises electrocardiograph (ECG) electrodes configured to measure one or more ECG signals of the body.

4. The transcutaneous sound sensor system of claim 1, wherein at least a portion of an outer surface of the in-vivo portion comprises a hydrophilic coating.

5. The transcutaneous sound sensor system of claim 1, wherein the second layer is a spiral layer wrapped around the innermost layer.

6. The transcutaneous sound sensor system of claim 1, wherein the second layer is a continuous, solid layer arranged around the innermost layer.

7. The transcutaneous sound sensor system of claim 1, wherein a third layer arranged around the second layer is a conductor.

8. The transcutaneous sound sensor system of claim 7, wherein the third layer is a spiral layer wrapped around the second layer.

9. The transcutaneous sound sensor system of claim 7, wherein a fourth layer arranged around the third layer is a protective layer.

10. The transcutaneous sound sensor system of claim 1, further comprising the electronics unit.

11. A transcutaneous sound sensor comprising:
a sound-sensing element implanted under skin of a subject and producing an electrical signal in response to a mechanical stress or strain on the sound-sensing element;
a proximal end disposed external to the skin of the subject to be releasably and communicatively coupled to an electronics unit, the proximal end comprising an electrical insulation layer disposed at an end of the sound-sensing element; and
a protective layer arranged around the sound-sensing element.

12. The transcutaneous sound sensor of claim 11, wherein the sound-sensing element and the electrical insulation layer surround core conductor.

13. The transcutaneous sound sensor of claim 12, wherein the sound-sensing element is spirally wrapped around the core conductor.

14. The transcutaneous sound sensor of claim 11, wherein a conductor layer is arranged around the sound-sensing element and the electrical insulation layer.

15. The transcutaneous sound sensor of claim 14, wherein conductor layer is spirally wrapped around the sound-sensing element.

16. The transcutaneous sound sensor of claim 14, wherein the protective layer surrounds the conductor layer.

17. The transcutaneous sound sensor of claim 11, wherein at least a portion of an outer surface of the transcutaneous sound sensor comprises a hydrophilic coating.

18. The transcutaneous sound sensor of claim 11, wherein the sound-sensing element is formed from a polarized polyvinylidene fluoride (PVDF) film, a PVDF copolymer film, or a piezoceramic material.

19. The transcutaneous sound sensor of claim 18, wherein the PVDF copolymer film includes PVDF-TrFE.

20. The transcutaneous sound sensor of claim 11, wherein the protective layer is formed from a biocompatible insulation material.

21. The transcutaneous sound sensor of claim 20, wherein the biocompatible insulation material is at least one of: a parylene, a silicon rubber, or ePTFE.

22. A method of treatment using a transcutaneous sound sensor system, the method comprising:
coupling an electronics unit to a sound sensor, the sound sensor configured to sense sounds originating from inside a subject, the sound sensor comprising an in-vivo portion arranged beneath a skin surface of the subject and an ex-vivo portion arranged exterior to the skin surface, wherein the sound sensor has a coaxial structure comprising multiple layers, an innermost layer of the sound sensor is a core conductor, a second layer of the coaxial structure arranged around the innermost layer at the in-vivo portion of the sound sensor includes a polarized piezo-polymer layer, and the second layer of the coaxial structure arranged around the innermost layer at the ex-vivo portion of the sound sensor includes an electrically insulating material;
receiving signals at the electronics unit corresponding to sound measurements sensed by the sound sensor; and
processing the received signals to determine characteristics of the sound measurements.

23. The method of claim 22, further comprising implanting the in-vivo portion beneath the skin surface and the ex-vivo portion exterior to the skin surface.

24. The method of claim 22, further comprising correlating the characteristics of the sound measurements to specific parts of the subject.

25. A transcutaneous sound sensor system comprising:
a mounting unit detachably connectable to an electronics unit and mountable on a skin of a body; and
a sound sensor configured to sense sounds originated from inside the body, the sound sensor comprising an in-vivo portion and an ex-vivo portion, the in-vivo portion being insertable through and placed beneath the skin of the body, wherein the in-vivo portion has a sound-sensing element that produces an electrical signal in response to a mechanical stress or strain on the sound-sensing element, wherein the ex-vivo portion is arrangeable exterior to the skin and is operably connected to the electronics unit when the electronics unit is connected to the mounting unit,
wherein the sound sensor has a coaxial structure comprising multiple layers, an innermost layer of the sound sensor is a core conductor, a second layer of the coaxial structure arranged around the innermost layer at the in-vivo portion of the sound sensor includes a piezoceramic layer, and the second layer of the coaxial structure arranged around the innermost layer at the ex-vivo portion of the sound sensor includes an electrically insulating material.

* * * * *